(12) United States Patent
Tanaka et al.

(10) Patent No.: US 6,300,498 B1
(45) Date of Patent: Oct. 9, 2001

(54) SUBSTITUTED AMMONIUM SALT OF 1,5'-BITETRAZOLE

(75) Inventors: Hiroaki Tanaka; Kunihiro Shimamoto; Atuhiro Onishi, all of Takasago (JP)

(73) Assignee: Toyo Kasei Kogyo Company Limited, Osaka-fu (JP)

( * ) Notice: Subject to any disclaimer, the term of this patent is extended or adjusted under 35 U.S.C. 154(b) by 0 days.

(21) Appl. No.: 09/360,109

(22) Filed: Jul. 23, 1999

(51) Int. Cl.[7] ............. C07D 403/04; C07D 257/06; C06B 23/00
(52) U.S. Cl. ............. 544/185; 149/36; 544/196; 544/336; 544/358; 544/410; 548/251
(58) Field of Search ............. 149/36; 544/185, 544/196, 336, 358, 410; 548/251

(56) References Cited

U.S. PATENT DOCUMENTS

| | | | |
|---|---|---|---|
| 5,439,251 | 8/1995 | Onishi et al. | 280/741 |
| 5,682,014 | * 10/1997 | Highsmith et al. | 149/36 |
| 5,872,329 | * 2/1999 | Burns et al. | 149/36 |

FOREIGN PATENT DOCUMENTS 10-298168 * 11/1998 (JP) .

* cited by examiner

*Primary Examiner*—Edward A. Miller
(74) *Attorney, Agent, or Firm*—Kubovcik & Kubovcik

(57) ABSTRACT

The 1,5'-bitetrazole of the invention comprises 1,5'-bitetrazole, and ammonia or an amine. The 1,5'-bitetrazole of the invention decomposes sharply and generates a non-toxic gas.

1 Claim, 3 Drawing Sheets

SUBSTITUTED AMMONIUM SALT OF 1,5'-BITETRAZOLE

BACKGROUND OF THE INVENTION

The present invention relates to novel 1,5'-bitetrazole compounds and processes for their production.

The present invention also relates to gas generating agents containing the 1,5'-bitetazole compounds.

The present invention further relates to foaming agents for precision molding of resins, foaming agents for reducing weight of molded articles, smoking agents for effectively diffusing chemicals such as agricultural chemicals or insecticides, and air bag gas generating agents.

It is difficult td mold crystalline resins into the shape defined by a mold, since they crystallize and shrink upon cooling after molding. Conventionally, for precision molding of crystalline resins, apparent shrinkage is empirically inhibited by using specially devised molds, which, however, cannot accomplish complete precision molding. Accordingly, additional techniques for further reducing shrinkage of molded articles are employed, which include physical blowing of gas into the core portion of molded articles (Japanese Examined Patent Publications Nos. 41264/1973 and 14968/1982), and addition of chemical foaming agents (Japanese Unexamined Patent Publications Nos. 129563/1975, 12864/1978 and 61435/1981, and U.S. Pat. No. 4,871,861). In conventional techniques, azodicarbonamide (ADCA) has been used widely for a long period of time, mainly for foam molding of resins.

ADCA, although utilized widely as a gas generating agent, is not wholly satisfactory for use in precision molding or high-foam molding for weight reduction, because it has too broad a decomposition temperature range relative to the molding temperature and causes air bubbles on the surface of molded articles, which impair the appearance. Moreover, decomposition gases and residues of ADCA contain toxic substances such as ammonia, biurea or isocyanuric acid, and thus are harmful to humans and animals and the environment. Further, the decomposition residue contaminates molds, decreasing the molding efficiency and yield of molded articles.

To solve the above problems, use of tetrazoles as gas generating agents was proposed. Tetrazoles, which decompose completely, are free from the above problems. However, since high decomposability means low stability, tetrazoles are highly sensitive to friction or other physical factors, lacking handling safety.

Further, although air bag gas generating agents and smoking agents are required to be harmless to humans and animals, safe, and odorless, conventional air bag gas generating agents and smoking agents do not fully satisfy these requirements.

SUMMARY OF THE INVENTION

An object of the invention is to provide a novel 1,5'-bitetrazole compound which is highly sensitive only to temperature and which decomposes sharply, i.e., decomposes in a narrow temperature range, and generates a non-toxic gas.

Another object of the invention is to provide a gas generating agent which is highly sensitive only to temperature and which decomposes sharply and generates a non-toxic gas.

The present inventors did extensive research to achieve the above objects and directed their attention to 1,5'-bitetrazole which leaves substantially no residue upon decomposition. They found that ammonia or amine can be used to reduce the physical sensitivities of 1,5'-bitetrazole. The present invention has been accomplished based on this novel finding.

The present invention provides the following 1,5'-bitetrazole, processes for their production, and gas generating agents containing the.

1. A 1,5'-bitetrazole represented by the formula (1):

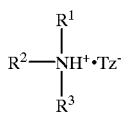

(1)

wherein $Tz^{31}$ represents

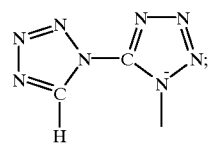

$R^1$, $R^2$ and $R^3$ are the same or different and each represent a hydrogen atom; $C_{1-10}$ alkyl which may be substituted by amino, di($C_{1-4}$ alkyl)amino, $C_{1-8}$ alkoxy, hydroxy or phenyl; $C_{3-20}$ alkenyl; phenyl; —C(=NH)NH$_2$; —C(=NH)NHNH$_2$; —C(=NH)NHCN; triazolyl; amino; carbamoyl; triazinyl which may be substituted by amino and methyl; —NHCS;

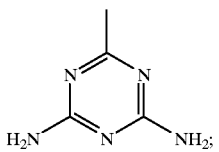

or —$R^4$—$NH_3^+$ $Tz^-$ wherein $Tz^-$ is as defined above, $R^4$ represents a single bond, $C_{2-6}$ alkylene, phenylene, —CO— or

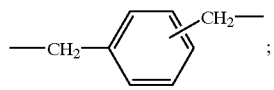

when $R^1$ is a hydrogen atom, $R^2$ and $R^3$ may be taken together with the nitrogen atom to which they are attached to form a 5- to 7-membered saturated heterocycle; when $R^1$ is a hydrogen atom, $R^2$ and $R^3$ may be taken together to form

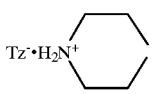

or

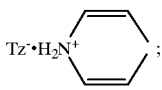

and $R^1$, $R^2$ and $R^3$ may be taken together to form

2. A process for producing a 1,5'-bitetrazole amine salt according to Item 1 comprising the step of reacting 1,5'-bitetrazole or its alkali salt with ammonia or an or its carbonate or halide, the amine being represented by the formula:

$$R^5R^6R^7N \quad (2)$$

wherein $R^5$, $R^6$ and $R^7$ are the same or different and each represent a hydrogen atom; $C_{1-10}$ alkyl which may be substituted by amino, di($C_{1-4}$ alkyl)amino, $C_{1-8}$ alkoxy, hydroxy or phenyl; $C_{3-20}$ alkenyl; phenyl; —C(=NH)NH$_2$; —C(=NH)NHNH$_2$; —C(=NH)NHCN; triazolyl; amino; carbamoyl; triazinyl which may be substituted by amino and methyl; —NHCS;

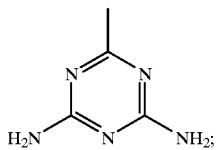

or —$R^8$—NH$_2$ wherein $R^8$ represents a single bond, $C_{2-6}$ alkylene, phenylene, —CO— or

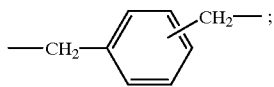

when $R^5$ is a hydrogen atom, $R^6$ and $R^7$ may be taken together with the nitrogen atom to which they are attached to form a 5- to 7-membered saturated heterocycle; when $R^5$ is a hydrogen atom, $R^6$ and $R^7$ may be taken together to form

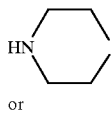

or

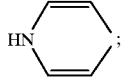

and $R^5$, $R^6$ and $R^7$ may be taken together to form

3. A gas generating agent containing a 1,5'-bitetrazole according to Item 1.
4. A foaming agent for molding resins, which contains a 1,5'-bitetrazole according to Item 1.
5. An air bag gas generating agent containing a 1,5'-bitetrazole according to Item 1.
6. A smoking agent for diffusing chemicals, which contains a 1,5'-bitetrazole according to Item 1.

The 1,5'-bitetrazole amine salt of the invention comprises 1,5'-bitetrazole, and ammonia or an amine.

Useful amines include monomethylamine, monoethylamine, n-propylamine, isopropylamine, n-butylamine, sec-butylamine, t-butylamine, n-hexylamine, n-octylamine, 2-ethylhexylamine, oleylamine, allylamine, 3-dimethylaminopropylamine, 3-dibutylaminopropylamine, 3-methoxypropylamine, 3-ethoxypropylamine, 2-ethylhexyloxypropylamine, methyliminobispropylamine, cyclohexylamine, aniline, benzylamine, phenethylamine, dicyandiamide, guanidine, aminoguanidine, aminotriazole, monoethanolamine and like primary monoamines; ethylenediamine, hexamethylenediamine, phenylenediamine, xylenediamine, xylylenediamine, acetoguanamine, hydrazine, urea, carbohydazide, thiocarbohydrazide, N-acetyl-m-phenylenediamine, 2,4-diamino-6-methyl-symtriazine, 1,4-bis(3-aminopropyl)piperazine and like primary diamines; melamine and like primary triamines; dimethylamine, diethylamine, dicyclohexylamine, di-2-ethylhexylamine, diethanolamine, piperazine, piperidine, diphenylamine and like secondary monoamines or secondary diamines; and trimethylamine, triethylamine, N,N,N',N'-tetramethylethylenediamine, hexamethylenetetramine, pyridine, N,N-dimethylaniline, N,N-dimethylcyclohexyl-amine, triethanolamine and like tertiary amines.

The process for producing the novel 1,5'-bitetrazole of the invention comprises the steps of dissolving 1,5'-bitetrazole or its alkali metal salt in water, an alcohol (preferably a $C_{1-3}$ alcohol) or dimethylformamide (DMF), and adding ammonia or the above amine or its carbonate or halide in an equivalent amount relative to the 1,5'-bitetrazole or its alkali metal salt, followed by stirring. When an alkali metal salt of 1,5'-bitetrazole and an amine halide are used, it is preferable to select such a combination that the alkali metal halide produced as a byproduct is soluble in water, alcohol or DMF, so that 1,5'-bitetrazole can be easily obtained by collecting crystals by filtration.

The reaction is carried out at preferably 0 to 100° C., more preferably 20 to 60° C., for a period of preferably 0.5 to 10 hours, more preferably 1 to 3 hours.

The 1,5'-bitetrazole is a novel substance which has low detonability and high stability against physical shocks, i.e., low sensitivity to impact or friction. Unlike ADCA, the 1,5'-bitetrazole is free from the problems of toxic decomposition gas or residue, since it decomposes completely and generates a nontoxic gas. Therefore, it is usable as an air bag gas generating agent or a smoking agent. Moreover, since the compound decomposes sharply, its use as a foaming agent, for example in injection molding, enables formation of a smooth skin layer which cannot be obtained by use of ADCA or like substance, and achieves precision molding free from sinkmarks or warpage.

BEST MODE FOR CARRYING OUT THE INVENTION

Figure 1:
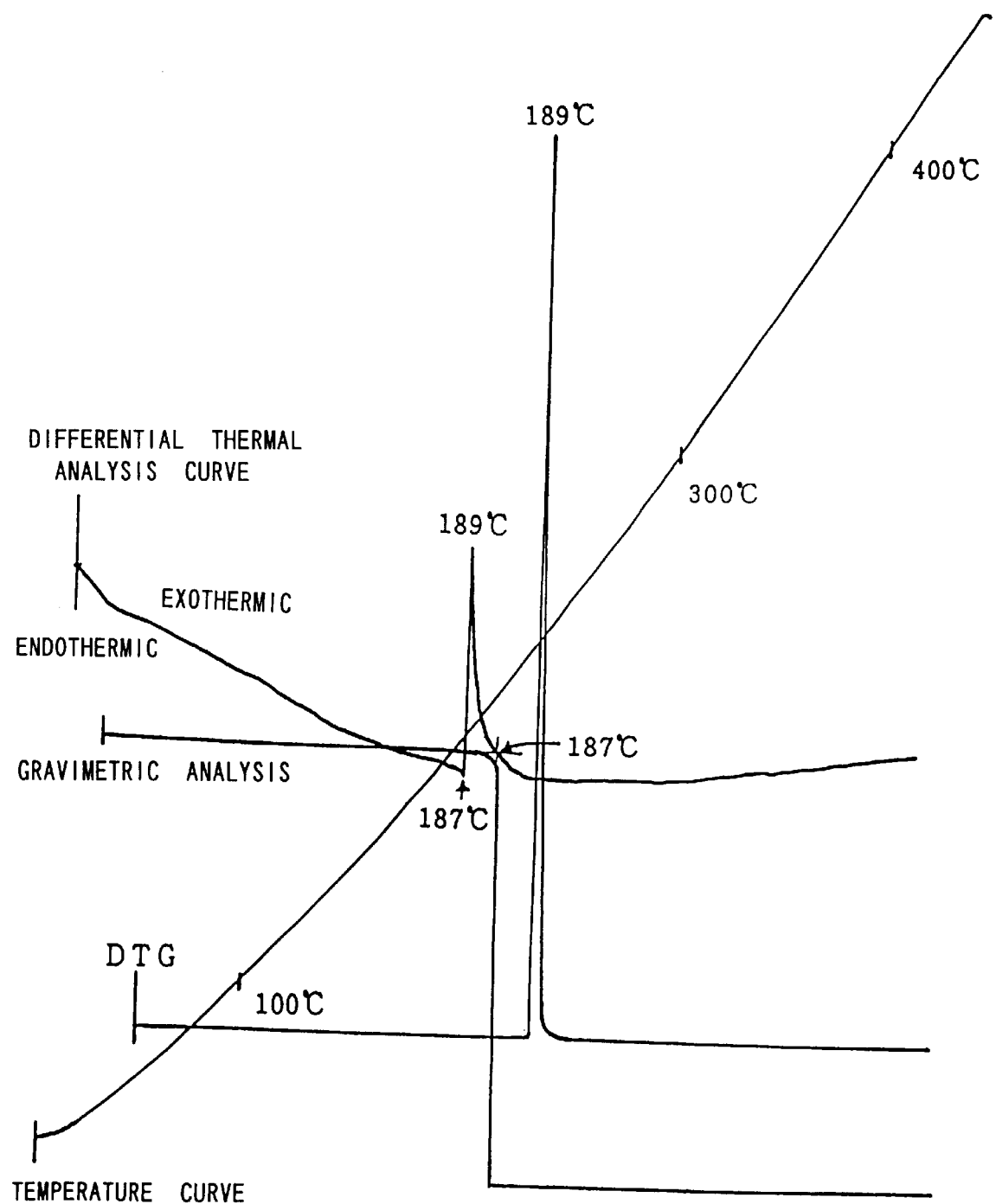
FIG. 1 shows the result of differential thermal analysis of 1,5'-bitetrazole guanidine salt as an embodiment of the invention.
Figure 2:
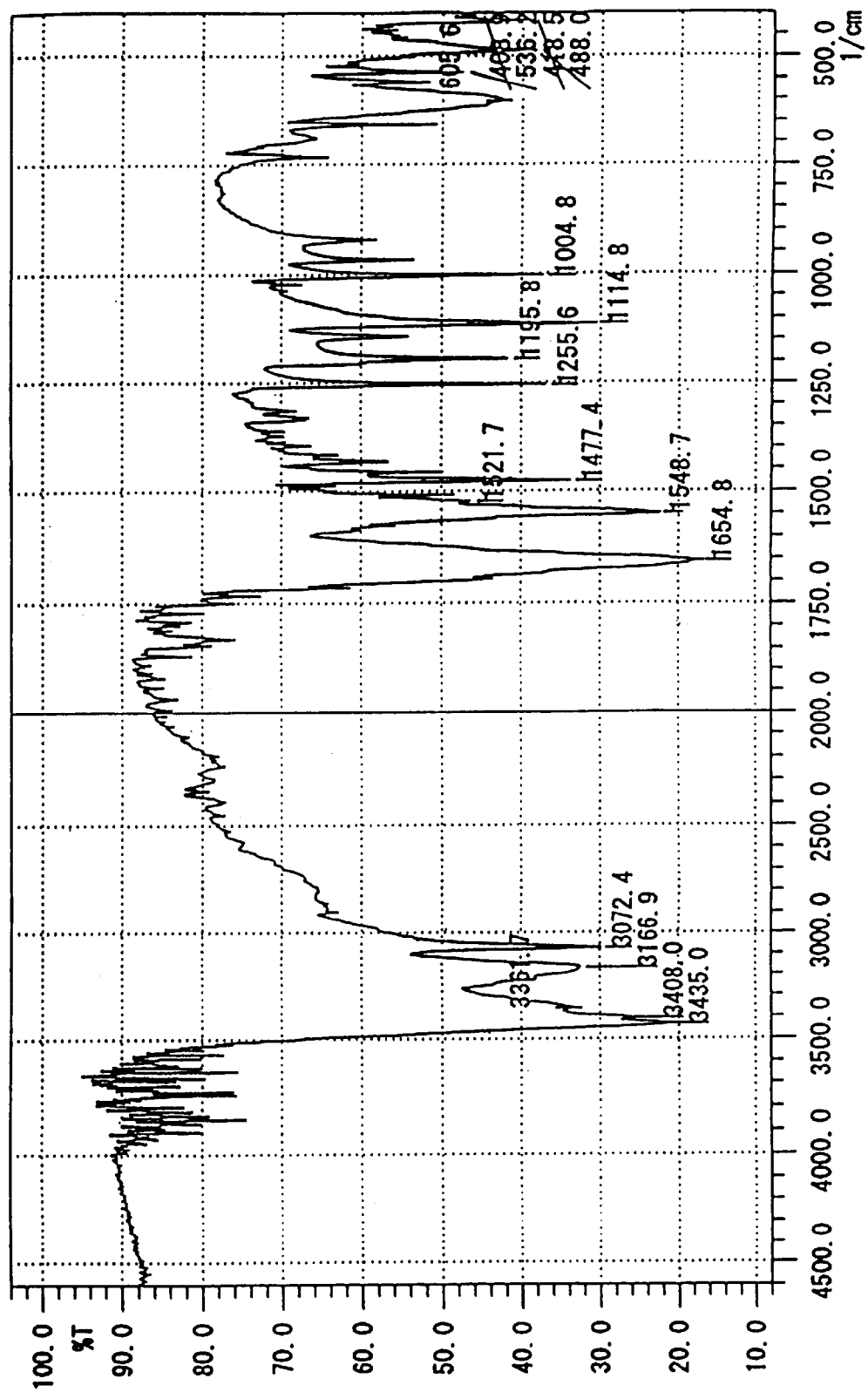
FIG. 2 shows the infrared absorption spectrum of 1,5'-bitetrazole guanidine salt as an embodiment of the invention.
Figure 3:
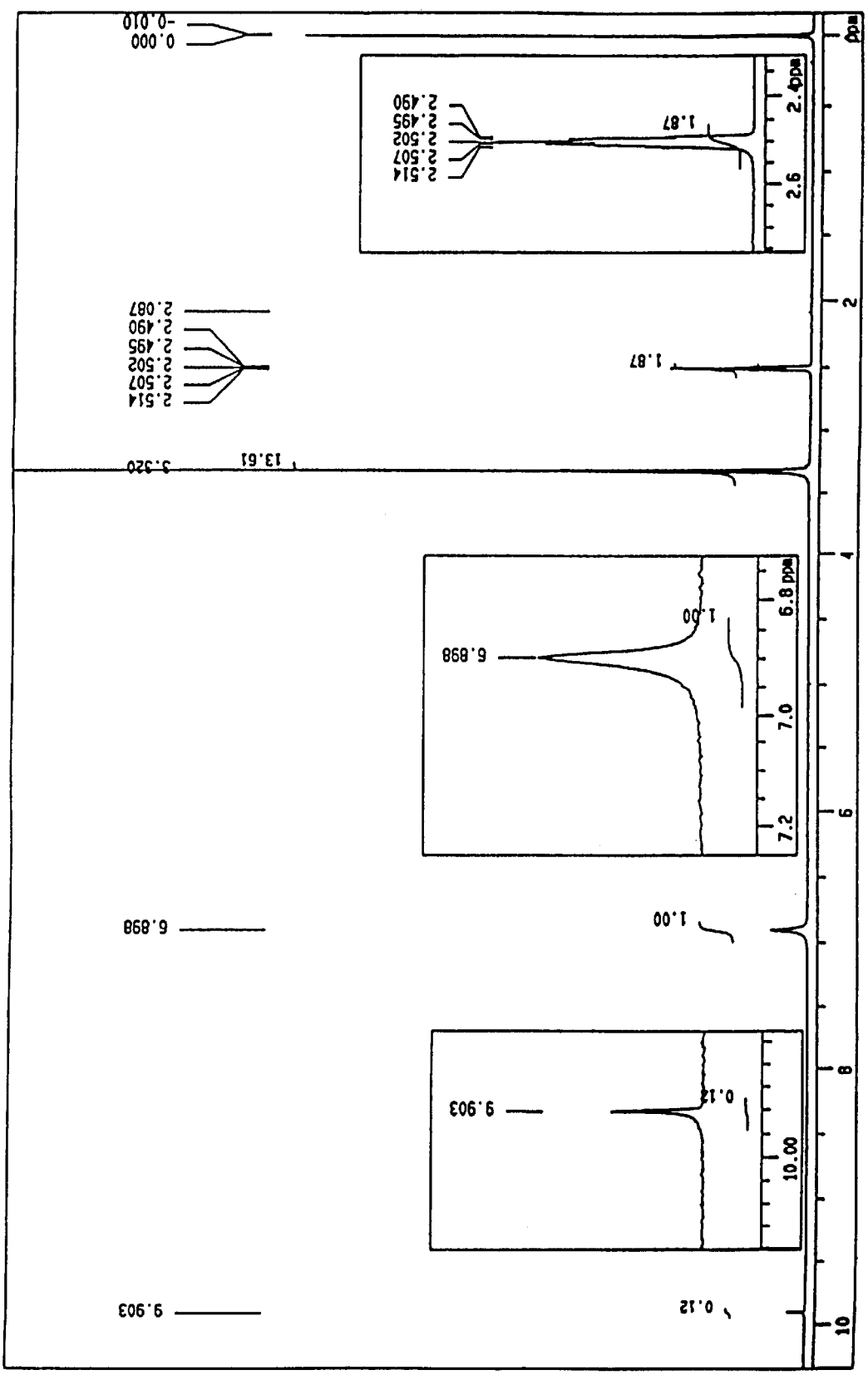
FIG. 3 shows the result of NMR analysis of 1.5'-bitetrazole guanidine salt as an embodiment of the invention.

The following examples are intended to illustrate the present invention in further detail.

EXAMPLE 1

A 500-ml, four-necked flask equipped with a stirrer and thermometer was set in an oil bath and charged with 50 g (0.362 moles) of 1,5'-bitetrazole (molecular weight: 138.09), followed by addition of 300 ml of water. The mixture was heated to 40° C., and 15.6 g (0.181 moles) of piperazine (molecular weight: 86.14) was added with stirring. Simultaneously with addition of the piperazine, crystals formed and the reaction mixture became pale yellow. The reaction mixture was cooled to room temperature with stirring, and subjected to suction filtration using a No. 2 filter paper, whereby 1,5'-bitetrazole piperazine salt (molecular weight: 362.32) was obtained in a yield of 85%.

EXAMPLE 2

2 g of 1,5'-bitetrazole was measured out into a 50-ml beaker, and dissolved by addition of 50 ml of methanol. 0.87 g of saturated aqueous ammonia was added, followed by thorough stirring. The methanol was allowed to evaporate to collect crystals, which were then washed with acetone and analyzed.

EXAMPLE 3

2 g of 1,5'-bitetrazole was measured out into a 50-ml beaker, and dissolved by addition of 50 ml of methanol. 10 ml of water and 1.37 g of benzylamine were added in this order. Crystals formed were collected and washed in the same manner as in Example 2, dried and analyzed.

EXAMPLE 4

1,5'-bitetrazole were obtained using amines other than those used in Examples 1, 2 and 3 and following the procedure of Example 1, 2 or 3.

EXAMPLE 5

The 1,5'-bitetrazole obtained in Examples 1 to 4 were subjected to determination of melting point and decomposition temperature, elementary analysis, infrared absorption analysis, and NMR analysis. The results are shown in Tables 1 to 8.

In the column of "decomposition" in Tables 1 and 2, "sharp" indicates that the decomposition occurred in a narrow temperature range, while "broad" indicates that the decomposition occurred over a broad temperature range.

TABLE 1

Melting Point and Decomposition Temperature
Primary Amine Salt

| Amine salt | M.P. (° C.) | Decomp. Temp. (° C.) | Boiling Point/ Sublimation Temp. (° C.) | Decomposition |
|---|---|---|---|---|
| 1,5-BHT·H$_2$O | — | 148 | | sharp |
| Ammonium | — | 185 | | sharp |
| Monomethylamine | 159 | 170 | | sharp |
| Ethylamine | 123 | 176 | | broad |
| n-Propylamine | — | 206 | | sharp |
| Isopropylamine | — | 218 | 258 | broad |
| sec-Butylamine | 168 | 197 | | broad |
| t-Butylamine | 145 | 187 | | broad |
| n-Hexylamine | — | 181 | | sharp |
| n-Octylamine | 93 | 185 | | broad |
| 2-Ethylhexylamine | 85 | 185 | | broad |
| Oleylamine | 91 | 188 | | broad |

TABLE 1-continued

Melting Point and Decomposition Temperature
Primary Amine Salt

| Amine salt | M.P. (° C.) | Decomp. Temp. (° C.) | Boiling Point/ Sublimation Temp. (° C.) | Decomposition |
|---|---|---|---|---|
| Allylamine | — | 209 | | sharp |
| Cyclohexylamine | 159 | 189 | | broad |
| Monoethanolamine | 125 | 169 | | sharp |
| Aniline | 132 | 206 | | broad |
| Benzylamine | 135 | 185 | | broad |
| Phenethylamine | 155 | 186 | | broad |
| Guanidine | 187 | 189 | | sharp |
| Aminoguanidine | 174 | 177 | | sharp |
| Dicyandiamide | — | 201 | | sharp |
| 3-Amino-1H-1,2,4-triazole | — | 167 | | sharp |
| Ethylenediamine | — | 185 | | sharp |
| Hexamethylenediamine | 141 | 172 | | sharp |
| m-Phenylenediamine | — | 201 | 233 | broad |
| m-Xylylenediamine | 166 | 186 | | broad |
| Hydrazine | 144 | 178 | | broad |
| 1-Urea | 131 | 149 | 217 | broad |
| 2-Urea | 119 | 151 | 215 | broad |
| Thiocarbohydrazide | 141 | 194 | | sharp |
| Melamine 1/3 | 190 | 255 | 311 | broad |
| Melamine 2/3 | 189 | 251 | 305 | broad |
| Melamine 1/1 | — | 256 | 326 | broad |

Notes:
(1) In Tables 1 and 2, "—" indicates that no clear melting point was found by the determination.
(2) "1,5-BHT" indicates 1,5'-bitetrazole. The same applies hereinafter.

TABLE 2

Melting Point and Decomposition Temperature
Secondary and Tertiary Amine Salts

| Amine salt | M.P. (° C.) | Decomp. Temp. (° C.) | Boiling Point/ Sublimation Temp. (° C.) | Decomposition |
|---|---|---|---|---|
| Dimethylamine | 134 | 152 | | broad |
| Piperazine | — | 205 | | sharp |
| Piperidine | — | 183 | | broad |
| Diphenylamine | 140 | 157 | | broad |
| Trimethylamine | — | 204 | | sharp |
| Hexamethylenetetramine | 148 | 178 | | broad |

TABLE 3

Elementary Analysis
Primary Amine Salt

| | C | | H | | N | |
|---|---|---|---|---|---|---|
| Amine Salt | Calcd. | Found | Calcd. | Found | Calcd. | Found |
| 1,5-BHT·H$_2$O | 15.39 | 15.42 | 2.58 | 2.52 | 71.78 | 71.25 |
| t-Butylamine | 34.12 | 35.57 | 6.20 | 6.24 | 59.68 | 58.63 |
| n-Hexylamine | 44.16 | 33.21 | 7.16 | 5.89 | 52.68 | 59.86 |
| n-Octylamine | 44.93 | 43.53 | 7.92 | 7.74 | 47.15 | 49.84 |
| 2-Ethylhexylamine | 44.93 | 44.59 | 7.92 | 8.07 | 47.15 | 47.50 |
| Oleylamine | 59.23 | 58.88 | 9.69 | 10.12 | 31.08 | 30.64 |
| Allylamine | 30.77 | 29.53 | 4.65 | 4.59 | 64.58 | 63.66 |
| Cyclohexylamine | 40.50 | 40.81 | 6.37 | 6.48 | 53.13 | 52.39 |
| Monoethanolamine | 24.12 | 24.60 | 4.55 | 4.60 | 63.29 | 62.00 |
| Aniline | 41.56 | 41.80 | 3.92 | 4.01 | 54.52 | 54.29 |
| Benzylamine | 44.08 | 44.92 | 4.52 | 4.51 | 51.40 | 51.81 |

TABLE 3-continued

Elementary Analysis
Primary Amine Salt

| Amine Salt | C Calcd. | C Found | H Calcd. | H Found | N Calcd. | N Found |
|---|---|---|---|---|---|---|
| Phenethylamine | 46.33 | 46.38 | 5.05 | 5.20 | 48.62 | 48.00 |
| Guanidine | 18.28 | 19.07 | 3.58 | 3.43 | 78.15 | 78.63 |
| Arninoguanidine | 16.98 | 16.75 | 3.80 | 4.11 | 79.22 | 79.77 |
| Dicyandiamide | 21.62 | 21.58 | 2.72 | 3.00 | 75.65 | 74.21 |
| 3-Amino-1H-1,2,4-triazole | 23.08 | 22.80 | 2.91 | 2.88 | 74.01 | 74.23 |
| Ethylenediamine | 21.43 | 20.90 | 3.60 | 4.05 | 74.96 | 75.02 |
| Hexamethylene-diamine | 37.79 | 36.21 | 7.13 | 7.08 | 55.08 | 55.32 |
| m-Phenylenediamine | 39.02 | 38.68 | 4.09 | 3.81 | 56.88 | 57.01 |
| m-Xylylenediamine | 34.95 | 34.56 | 3.91 | 4.05 | 61.14 | 59.48 |
| Hydrazine | 15.59 | 15.39 | 2.62 | 2.43 | 81.80 | 82.56 |
| 1-Urea | 18.19 | 17.85 | 3.05 | 2.93 | 70.69 | 70.76 |
| 2-Urea | 18.61 | 18.78 | 3.90 | 3.87 | 65.10 | 66.17 |
| Thiocarbohydrazide | 15.71 | 15.38 | 2.64 | 3.09 | 73.27 | 71.68 |
| Melamine 1/3 | 20.00 | 20.00 | 2.44 | 2.50 | 77.76 | 78.00 |
| Melamine 2/3 | 20.90 | 20.17 | 2.51 | 2.60 | 76.60 | 75.80 |
| Melamine 1/1 | 22.73 | 22.61 | 3.05 | 2.98 | 74.22 | 73.99 |

TABLE 4

Elementary Analysis
Secondary and Tertiary Amine Salts

| Amine Salt | C Calcd. | C Found | H Calcd. | H Found | N Calcd. | N Found |
|---|---|---|---|---|---|---|
| Dimethylamine | 26.23 | 25.37 | 4.95 | 4.50 | 68.82 | 69.07 |
| Piperazine | 26.52 | 26.51 | 3.89 | 4.11 | 69.58 | 68.27 |
| Piperidine | 37.66 | 37.43 | 5.87 | 5.97 | 56.47 | 55.97 |
| Diphenylamine | 54.72 | 55.85 | 4.26 | 4.11 | 42.17 | 41.57 |
| Trimethylamine | 30.45 | 30.17 | 5.62 | 5.49 | 63.92 | 63.15 |
| Hexamethylene-tetramine | 34.53 | 34.14 | 5.07 | 5.11 | 54.83 | 59.01 |

TABLE 5

Infrared Spectroscopic Analysis
Primary Amine Salt

| Amine Salt | Characteristic Absorption (cm$^{-1}$) |
|---|---|
| Ammonium | vNH2856.5 |
| Monomethyl-amine | (N—CH3) vasCH 2879.5, vaCH 2758.0 |
| | (N—CH3) δasCH 1461.9. δsCH 1380.0 |
| | (—NH3+) δasNH 1544.9. δsNH 1494.7 |
| Ethylamine | (—CH3) vasCH 2999.1. (CH2) vasCH2 2912.3, vsCH2 2912.3 |
| | (—CH3) δasCH 1463.9, δsCH 1377.5 |
| | (—NH3+) δasNH 1571.9, δsNH 1491.6 |
| n-Propylamine | (—CH3) vasCH 2977.9, (CH2) vasCH2 2906.7, vsCH2 2846.9 |
| | (—CH3) δasCH 1460.0, δsCH 1380.6 |
| | (—NH3+) δasNH 1606.6, δsNH 1514.4 |
| Isopropylamine | (—CH3) vasCH 2977.9, (CH2) vasCH2 2906.7, vsCH2 2846.9 |
| | (—CH3) δasCH 1460.0, δsCH 1380.6 |
| | (—NH3+) δasNH 1589.2, δsNH 1514.4 |
| sec-Butylamine | (—CH3) vasCH 2977.9, (—CH3) δasCH 1460.0, δsCH 1387.6 |
| | (—CH—(CH3) 2) skeleton 1187.6 |
| | (—NH3+) δasNH 1589.2, δsNH 1514.4 |
| t-Butylamine | (—CH3) vasCH 2970.2. vsCH 2883.4 |
| | (—C—(CH3) 3) skeleton 1262.0, 1218.9, 964.1 |

TABLE 5-continued

Infrared Spectroscopic Analysis
Primary Amine Salt

| Amine Salt | Characteristic Absorption (cm$^{-1}$) |
|---|---|
| n-Hexylamine | (—CH3) vasCH 3002.4, (GH2) vasCH2 2979.8, vsCH2 2860.2 |
| | (—CH3) δasCH 1458.1, δsCH 1370.8, —CH2—rocking 708.1 |
| | (—NH3+) δasNH 1610.0, δsNH 1513.2 |
| n-Octylamine | (—CH3) vasCH 2954:5, vsCH2 2856.4, (CH2) vasCH2 2918.1 |
| | vasCH2 2823.6, (—CH3) δasCH 1461.9, δsCH 1376.8 |
| | (—NH3+) δasNH 1604.7, δsNH 1500.5 |
| 2-Ethylhexyl-amine | (—CH3) vasCH2962.5, vsCH2 2871.8, (CH2) vasCH2 2931.6 |
| | vasCH2 2856.4, (—CH3) δasCH 1461.9, δsCH 1373.2 |
| | (—NH3+) δasNH 1618.4, δsNH 1508.2 |
| Oleylamine | (—CH3) vasCH 2952. 2, (CH2) vasCH2 2918. l, vsCH2 2850. 6 |
| | (CH3) δasCH 1463.9, δsCH 1372.1, —CH2—C=C—1435.4 |
| | (—NH3+) δasNH 1606.6, δsNH 1506.3 |
| Allylamine | (—C=CH) vCH 3023.9, (CH2) vasCH2 2919.8, vsCH2 2837.3 |
| | (—C=C—) vC=C 16.07.7, δ in plane CH 1441.4, δ out of plane CH 863.6 |
| Cyclohexyl-amine | (CH2) vasCH2 2935.5, vsCH2 2862.2 |
| | (—CH2) δCH scissors 1454.2 |
| | (—NH3+) δasNH 1591.2, δsNH 1488.0 |
| Monoethanol-amine | (CH2) vasCH2 2933.5, vsCH2 2879.5 |
| | (—CH2) δCH, scissors 1479.3 |
| | (—NH3+) δasNH 156.4, δsNH 1502.4 |
| Aniline | vCH 3047.8~2574.8, δ out of plane CH 1967.7, 1831.3, 1751.0 1647.1 |
| | (—NH3+) δasNH 1596.8, δsNH 1498.6 |
| Benzylamine | (—CH2—) δ scissors CH 1456.2 |
| | (—NH3+) δasNH 1575.0, δsNH 1495.2 |
| | (—CH2—) vasCH 2929.7, vout of plane CH 1955.7, 18380.4, 1750.0 |
| Phenethyl-amine | (—CH2—) δ scissors CH 1460.0 |
| | (—NH3+) δasNH 1583.7, δsNH 1496.7 |
| Guanidine | vNH 3435.0~3361.7 |
| | vC=N 1654.8 |
| Aminoguanidine | vNH 3448.5~3260.7 |
| | vC=N 1674.1, (—NH3+) δasNH 1544.9, δsNH 1453.3 |
| Dicyandiamide | vNH 3438.8—3260.7, vC=N 2193.8, 2167.5 |
| | vC=N 1689.5, 1641.3 |
| 3-Amino-1H-1,2,4-triazole | vNH 3369.4~3265.3, vC=N 1679.9, 1647.1 |
| | (—NH3+) δasNH 1556.4, δsNH 1505.9 |
| Ethylenediamine | vNH 3456.2~3074.3.(—NH3+) δasNH 1624.4 |
| | (—NH2—) vasCH 2943.4, vsCH 2883.4, scissors CH 1455.7 |
| Hexamethylene-diamine | vNH 3433.0~3026.3, (—NH3+) δasNH 1556.4, δsNH 15U5.9 |
| | (—CH2—) vasCH 2935.4, vsCH 2868.0, δ scissors CH 1463.9 |
| m-Phenylene-diamine | vNH 3476.1~3080.1, (—NH3+) δasNH 1596.8.δsNH 1498.6 |
| | vCH 3047.8~2574.8, δ out of plane CH 1967.7, 1831.3, 1751.0, 1647.1 |
| m-Xylylene-diamine | vCH 3448.5~3023.9, (—NH3+) δasNH 1595.7, δsNH 1504.4 |
| | (overlapped with Ph nucleus) δCH out of plane 1649.0 |
| | (—CH2—) vasCH 2918.9, vCH 2894.7, δ scissors CH 1479.3 |
| Hydrazine | vNH 3325.0~3055.0 |
| | (—NH3+) δasNH 1610.5, δsNH 1519.8 |
| Urea | vNH 3419.6~3095.5, (—NH3+) δasNH 1593.1, δsNH 1505.9 |
| | vC=O non—association 1697.2, |
| | vC=O association 1652.9 |
| Thiocarbo-hydrazide | vNH 3211.3, (—N3+) δasNH 1527.5, δsNH 15U5.9 |
| | vC=O non—association 1625.9 |
| | δC=S 1527.5, 1279.9, 1120.6, 931.6, 767.9 |

TABLE 5-continued

Infrared Spectroscopic Analysis
Primary Amine Salt

| Amine Salt | Characteristic Absorption (cm⁻¹) |
|---|---|
| Melamine 1/3 | νNH 3461.7~3328.9, (—NH2) δ in-plane scissors NH 1668.3, 1552.6 (—NH3+) δasNH 1614.3, δsNH 1504.4 (—NH2) δ out-of-plane scissors NH 1094.5, 812.2 |
| Melamine 2/3 | νNH 3461.7~3334.7, (—NH2) δ in-plane scissors NH 1670.2, 1554.5 (—NH3+) δasNH 1612.4, δsNH 1506.3 (—NH2) δ out-of-plane scissors NH 1095.5, 812.2 |
| Melamine 1/3 | νNH 3469.7~3332.8, (—NH2) δ in-plane scissors NH 1664.5, 1552.6 (—NH3+) δasNH 1614.3, δsNH 1500.0 (—NH2) δ out-of-plane scissors NH 1022.7, 813.9 |

TABLE 6

Infrared Spectroscopic Analysis
Secondary and Tertiary Amine Salts

| Amine Salt | Characteristic absorption (cm⁻¹) |
|---|---|
| Dimethylamine | (—CH3) νasCH 2976.0, νsCH 2759.9, δasCH 1460.0, δsCH 1382.8 νCH 3406.7~3026.1, (—NH3+) δasNH 1544.9, δsNH 1494.7 |
| Piperazine | (—CH2) νasCH2 2950.9, νsCH2 2862.2, δsNH scissors 1460.0 NH 3236.8, 2758.0, δNH1608.9 |
| Piperidine | (—CH2) νasCH2 2950.9, νsCH2 2862.2, δCH scissors 1428.2 νNH 2753.6, 2526.3, 1607.7 |
| Diphenylamine | νNH 3419.6, (—NH3+) δasNH 1610.5, δsNH 1519.R νCH 3091.7, δ out of plane CH 1697.2, 1652.9, Ph nucleus 1593.1 |
| Trimethylamine | (—CH2) νasCH 3004.9, νsCH2 2756.1, δasNH 1460.0, δsCH 1384.0 νNH 3398.3~3246.8, (—NH+) δasNH 1544.9, δsNH 1494.7 |
| Hexamethylene-tetramine | νC—N 1238.1, δCH2 rocking 1008.7, 817.8, 657.7 |

TABLE 7

NMR Analysis
Primary Amine Salt

| Amine Salt | (ppm) | Solvent |
|---|---|---|
| Ammonium | δ9.95 (s, 1H) | D₂O |
| Monomethylamine | δ9.7 (s, 1H), δ2.75 (S, 3H) | D₂O |
| Ethylamine | δ9.7 (s, 1H), δ3.35–2.95 (q, 2H), δ1.5–1.25 (t, 3H) | D₂O |
| n-Propylamine | δ9.0 (s, 1H) δ2.5–2.1 (t, 2H) δ1.4–0.8 (2H), δ0.6–0.3(t, 3H) | D₂O |
| Isopropylamine | δ9.1 (s, 1H), δ1.0 (d, 6H).6 3.5–3.0 (1H) | D₂O |
| n-Butylamine | δ9.9 (s, 1H), δ3.3 (9H) | DMSO |
| sec-Butylamine | δ9.9 (s, 1H), δ1.5(t, 2H), δ1.1(d, 6H), δ3.3 (1H) | DMSO |
| t-Butylamine | δ9.7 (s, 1H), δ1.4 (s, 9H) | D₂O |
| n-Hexylamine | δ9.9(s, 1H), δ1.5 (13H) | DMSO |
| n-Octylamine | δ9.7 (s, 1H), δ2.0–2.1 (n, 14H), δ0.8 (s, 3H) | D₂O |
| 2-Ethylhexyl-amine | δ9.7 (s, 1H), δ2.9–3.1 (d, 2H) δ1.5–1.0 (m, 6H), δ0.8–1.0(m, 6H) | D₂O |
| Oleylamine | δ9.7 (s, 1H), δ5.2 (s, 2H), 1.0 (s, 28H). δ0.7 (s, 3H) | DMSO |

TABLE 7-continued

NMR Analysis
Primary Amine Salt

| Amine Salt | (ppm) | Solvent |
|---|---|---|
| Allylamine | δ9.9 (s, 1H), δ5.3 (t, 2H), δ5.8(1H), δ3.4 (d, 2H) | DMSO |
| Cyclohexylamine | δ9.7 (s, 1H), δ3.4–3.0 (1H), δ2.2–1.0 (10H) | D₂O |
| Monoethanol-amine | δ9.0 (s, 1H), δ3.3–3.0 (t, 2H), δ2.7–2.4 (t, 12H) | D₂O |
| Aniline | δ9.2 (s, 1H), δ6.9 (s, 5H) | D₂O |
| Benzylamine | δ9.9 (s, 1H), δ7.4 (ph, 5H), δ4.1 (s, 2H) | DMSO |
| Phenethylamine | δ9.65 (s, 1H), δ7.25 (s, 5H), δ3.5–2.8 (dd, 4H) | D₂O |
| Guanidine | δ9.9 (s, 1H), δ6.9 (s, 1H), δ3.35 (s, 2H) | D₂O |
| Aminoguanidine | Hydrogen in amine cannot be independently determined | DMSO |
| Dicyandiamide | δ9.9 (s, 1H) | DMSO |
| 3-Amino-1H-1,2,4-triazole | δ8.1 (s, 1H) | D₂O |
| Ethylenediamine | δ9.7 (s, 2H), δ3.6 (s, 4H) | D₂O |
| Hexamethylene-diamine | δ9.7 (s, 2H), δ3.3–2.8 (4H), δ2.1–1.3 (4H) | D₂O |
| m-Phenylene-diamine | δ9.7 (s, 2H), δ7.6–7.2 (4H) | D₂O |
| m-Xylylenediamine | δ9.9 (s, 2H), δ7.5 (ph, 4H), δ4.1 (s, 4H) | DMSO |
| Hydrazine | δ9.7 (s, 2H), | D₂O |
| 1-Urea | δ10.1 (s, 1H), δ7.5 (s, 5H) | DMSO |
| 2-Urea | δ10.2 (s, 1H), δ8.2 (s, 6H) | DMSO |
| Thiocarbohydrazide | δ9.8 (s, 2H) | D₂O |
| Melamine 1/3 | δ9.8 (s, 3H), δ6.5 (s, 10H) | DMSO |
| Melamine 2/3 | δ7.3 (s, 2H), δ4.6 (s, 8H) | DMSO |
| Melamine 1/1 | δ8.0 (s, 1H), δ3.4 (s, 4H) | DMSO |

TABLE 8

NMR Analysis
Secondary and Tertiary Amine Salts

| Amine Salt | (ppm) | Solvent |
|---|---|---|
| Dimethylamine | δ9.7 (S, 1H), δ2.4 (s, 6H) | D₂O |
| Piperazine | δ9.7 (s, 1H), δ3.85 (s, 8H) | D₂O |
| Piperidine | δ9.7 (s, 1H), δ3.4–3.0 (t, 4H), δ2.0–1.6 (s, 6H) | D₂O |
| Diphenylamine | δ10.0 (s, 1H), δ7.2 (t, 4H) δ7.1 (d, 4H), δ6.8 (t, 2H) | DMSO |
| Trimethylamine | δ9.9 (s, 1H), δ2.8 (s, 9H) | DMSO |
| Hexamethylene-tetramine | δ9.7 (s, 1H), δ4.7 (s, 12H) | D₂O |

The above results reveal that the 1,5'-bitetrazole of the invention is a novel substance.

EXAMPLE 6

The crystals of 1,5'-bitetrazole piperazine salt obtained in Example 1 were finely ground in a mortar, added to a low-density polyethylene (melting point: 90° C.) in a proportion of 5 wt. % relative to the polyethylene, and extrusion-molded using an extruder at a resin temperature of 140° C., giving master chips having a diameter of about 3 mm and a length of about 3 mm.

EXAMPLE 7

The crystals of 1,5'-bitetrazole guanidine salt obtained in Example 4 were finely ground in a mortar, added to an acrylonitrile-styrene resin (AS resin; Vicat softening point: 104° C.) in a proportion of 5 wt. % relative to the resin, and extrusion-molded using an extruder at a resin temperature of 140° C., giving master chips having a diameter of about 3 mm and a length of about 3 mm.

EXAMPLE 8

The master chips obtained in Example 6 were added to a polypropylene resin to be molded, in a proportion of 2 wt. % relative to the resin, and injection-molded at 220° C. using a test mold measuring 3 mm thick, 100 mm wide and 100 mm long and having ribs with three different widths of 4 mm, 5 mm and 6 mm. The obtained molded article was compared with a blank molded article containing no foaming agent. The blank article had sinkmarks on the surface opposite to the ribbed surface and was commercially unacceptable, whereas the molded article containing the foaming agent of the present invention was completely free from sinkmarks.

EXAMPLE 9

The master chips obtained in Example 7 were added to a polyacetal resin to be molded, in a proportion of 2 wt. % relative to the resin, and injection-molded at 210° C. using a test mold measuring 3 mm thick, 100 mm wide and 100 mm long and having ribs with three different widths of 4 mm, 5 mm and 6 mm. The obtained molded article was compared with a blank molded article containing no foaming agent. The blank article had sinkmarks on the surface opposite to the ribbed surface and was commercially unacceptable, whereas the molded article containing the foaming agent of the present invention was completely free from sinkmarks and had a smooth skin layer.

COMPARATIVE EXAMPLE 1

Master chips were prepared in the same manner as in Example 6 except for using 20 wt. % of ADCA in place of the crystals of 1,5'-bitetrazole piperazine salt, and added to a polypropylene resin to be molded, in a proportion of 2 wt. % relative to the resin. The mixture was injection-molded at 220° C. using a test mold measuring 3 mm thick, 100 mm wide and 100 mm long and having ribs with three different widths of 4 mm, 5 mm and 6 mm. The obtained molded article was compared with a blank molded article containing no foaming agent and with the molded article of Example 8. The molded article obtained in this comparative example was satisfactorily foamed but had so-called "silver blisters", i.e., air bubbles on the surface. Also, the mold was severely contaminated when repeated test molding was carried out.

COMPARATIVE EXAMPLE 2

Master chips were prepared in the same manner as in Example 7 except for using 20 wt. % of ADCA in place of the crystals of 1,5'-bitetrazole guanidine salt, and added to a polyacetal resin to be molded, in a proportion of 2 wt. % relative to the resin. The mixture was injection-molded in the same manner as in Comparative Example 1. The obtained molded article was compared with a blank molded article and with the molded article of Example 9. The molded article obtained in this comparative example was satisfactorily foamed but had so-called "silver blisters", i.e., air bubbles on the surface, and did not have clearly defined edges. Also, the mold was severely contaminated when repeated test molding was carried out.

What is claimed is:

1. A substituted ammonium salt of 1,5'-bitetrazole represented by formula (1):

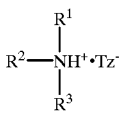
(1)

wherein $Tz^-$ represents

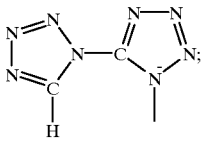

$R^1$, $R^2$, and $R^3$ are the same or different and each represent a hydrogen atom; $C_{1-10}$ alkyl which may be substituted by amino, di($C_{1-4}$ alkyl) amino, $C_{1-8}$ alkoxy, hydroxy or phenyl; $C_{3-20}$ alkenyl; phenyl; —C(=NH)NH$_2$; —C(=NH)NHNH$_2$; —C(=NH)NHCN; triazolyl; amino; carbamoyl; triazinyl which may be substituted by amino and methyl; —NHCS;

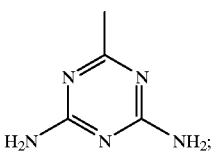

or —$R^4$—NH$_3^+$ $Tz^-$ wherein $Tz^-$ is as defined above, $R^4$ represents a single bond, $C_{2-6}$ alkylene, phenylene, —CO— or

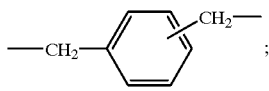

when $R^1$ is a hydrogen atom, $R^2$ and $R^3$ may be taken together with the nitrogen atom to which they are attached to form a 5— to 7—membered saturated heterocycle; when $R^1$ is a hydrogen atom, $R^2$ and $R^3$ may be taken together to form

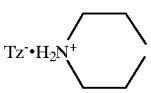

or

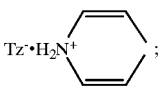

and $R^1$, $R^2$ and $R^3$ may be taken together to form

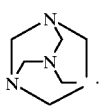

* * * * *